(12) United States Patent
Ikushima

(10) Patent No.: US 8,697,012 B2
(45) Date of Patent: Apr. 15, 2014

(54) HIGH-SPEED AUTOMATIC DISPENSING DEVICE WITH REPLACEABLE DISPENSING HEAD AND DISPENSING STATION

(75) Inventor: Kazumasa Ikushima, Tokyo (JP)

(73) Assignee: Musashi Engineering, Inc., Tokyo (JP)

( * ) Notice: Subject to any disclaimer, the term of this patent is extended or adjusted under 35 U.S.C. 154(b) by 1228 days.

(21) Appl. No.: 11/915,270

(22) PCT Filed: May 17, 2006

(86) PCT No.: PCT/JP2006/309817
§ 371 (c)(1),
(2), (4) Date: Oct. 3, 2008

(87) PCT Pub. No.: WO2006/123690
PCT Pub. Date: Nov. 23, 2006

(65) Prior Publication Data
US 2009/0129985 A1    May 21, 2009

(30) Foreign Application Priority Data

May 17, 2005 (JP) ................................. 2005-144762

(51) Int. Cl.
*B01L 3/02*     (2006.01)
*G01N 1/14*     (2006.01)

(52) U.S. Cl.
USPC ........... 422/511; 422/509; 422/510; 422/525; 73/864.14

(58) Field of Classification Search
USPC ................ 422/509, 511, 100, 525; 73/864.14
See application file for complete search history.

(56) References Cited

U.S. PATENT DOCUMENTS

| 6,182,719 | B1* | 2/2001 | Yahiro | 141/130 |
| 6,415,669 | B1* | 7/2002 | Carl | 73/864.14 |
| 6,575,209 | B2* | 6/2003 | Gora | 422/100 |
| 6,589,483 | B1 | 7/2003 | Maeda | |
| 6,846,680 | B2* | 1/2005 | Friswell et al. | 436/180 |
| 2002/0146353 | A1* | 10/2002 | Bevirt et al. | 422/100 |
| 2002/0176801 | A1* | 11/2002 | Giebeler et al. | 422/82.05 |
| 2002/0176803 | A1* | 11/2002 | Hamel et al. | 422/100 |
| 2004/0231438 | A1* | 11/2004 | Schwartz | 73/864.17 |

FOREIGN PATENT DOCUMENTS

| JP | 78935-1980 U | 5/1980 |
| JP | 5-87820 A | 4/1993 |
| JP | 7020010 A | 1/1995 |
| JP | 11-326341 A | 11/1999 |
| JP | 2001-33463 A | 2/2001 |
| JP | 2001-296303 A | 10/2001 |

OTHER PUBLICATIONS

International Search Report of PCT/JP2006/309817, date of mailing Aug. 1, 2006.

* cited by examiner

*Primary Examiner* — Jill Warden
*Assistant Examiner* — Brittany Fisher
(74) *Attorney, Agent, or Firm* — Westerman, Hattori, Daniels & Adrian, LLP

(57) ABSTRACT

A high-speed automatic dispensing apparatus capable of preparing samples under different conditions, minimizing waste liquid materials, and realizing high productivity. A dispensing station is also provided. The high-speed automatic dispensing apparatus with a replaceable dispensing head comprises a dispensing head including a plurality of pipettes, a pipette head to which one end of a plunger extending to pass through each pipette is fixed, and a head body part abutting against the pipette head and allowing the pipettes to pass therethrough, a pipette head moving mechanism vertically moving the pipette head, and a drive mechanism horizontally and vertically moving the dispensing head. The dispensing station includes the high-speed automatic dispensing apparatus.

10 Claims, 12 Drawing Sheets

AA Section

AASection phertiseplacement## HIGH-SPEED AUTOMATIC DISPENSING DEVICE WITH REPLACEABLE DISPENSING HEAD AND DISPENSING STATION

TECHNICAL FIELD

The present invention relates to a high-speed automatic dispensing apparatus with a replaceable dispensing head, which can prepare samples under different conditions and minimize waste liquid materials. The present invention also relates to a dispensing station.

BACKGROUND ART

Hitherto, in experiments of, for example, mixing chemical materials including medicines or mixing organisms and chemical materials in the field of biotechnology, samples have been prepared by sucking a target liquid material with a pipette and pouring the sucked liquid material into a test tube or a reagent bottle. With the progress of medicines and biotechnology, the number of prepared samples is drastically increased to such an extent that one pipette is not adaptable for preparing so many samples. For the purpose of increasing productivity, the number of holes formed in a dispense plate (microplate) to receive the dispensed liquid material is also increased from 96 per plate to four times, i.e., 384, in the so-called multihole plate. Recently, it has also been requested to prepare samples in different amounts or samples containing plural components. To meet those demands, a dispensing apparatus is proposed which can determine independently for each liquid dispensing portion whether a liquid is to be dispensed or not (Patent Document 1).

Patent Document 1: Japanese Patent Laid-Open No. H7-20010

DISCLOSURE OF THE INVENTION

Problems to be Solved by the Invention

When the amount of a liquid material sucked by a pipette is reduced, a tip is discarded together with the remaining liquid material. With the development of a multi-tip structure, however, a total amount of the discarded liquid material is increased correspondingly. If the liquid material is expensive, a material cost is also greatly increased with an increase in the amount of the discarded liquid material.

Further, when the number of pipettes mounted to a dispensing head and the number of holes formed in a dispense plate to receive the dispensed liquid material are in a 1:1 relation, samples under different conditions cannot be prepared in one dispense plate. Thus, increasing the number of pipettes mounted to the dispensing head is effective in preparing a large number of samples just under the same conditions, but it is not adapted for preparing samples under different conditions and lacks universality. On the other hand, reducing the number of pipettes is disadvantageous in not contributing to an improvement in efficiency of the operation and hence increasing the cost.

In view of the problems mentioned above, an object of the present invention is to provide a high-speed automatic dispensing apparatus capable of preparing samples under different conditions, minimizing waste liquid materials, and realizing high productivity, and to further provide a dispensing station.

Means for Solving the Problems

In the present invention, a dispensing head has such a structure that it is divided into a body part and a pipette head and only the pipette head is movable in the up-and-down direction. Further, the dispensing head is replaceable.

More specifically, a first aspect of the present invention resides in a high-speed automatic dispensing apparatus with a replaceable dispensing head, the dispensing apparatus comprising a dispensing head including a plurality of pipettes, a pipette head to which one end of a plunger extending to pass through each pipette is fixed, and a head body part abutting against the pipette head and allowing the pipettes to pass therethrough, a pipette head moving mechanism vertically moving the pipette head, and a drive mechanism horizontally and vertically moving the dispensing head.

According to a second aspect of the present invention, in addition to the first aspect of the present invention, the high-speed automatic dispensing apparatus further comprises a tip releasing plate abutting against the head body part, allowing the pipettes to pass therethrough, and being positioned near portions of the pipettes at which tips are attached to the pipettes, and the tips are released from the pipettes by moving the tip releasing plate downward.

According to a third aspect of the present invention, in addition to the second aspect of the present invention, the tip releasing plate is moved downward by a pushing member provided in said pipette head.

According to a fourth aspect of the present invention, in addition the second or third aspect of the present invention, the tip releasing plate has steps formed such that a step thickness is gradually increased from opposite end areas in the lengthwise direction toward a central area.

A fifth aspect of the present invention resides in a dispensing station comprising the high-speed automatic dispensing apparatus with the replaceable dispensing head according to any of the first to fourth aspects, a tip box on which a plurality of tips are arranged at a certain interval, a tip box palette on which the tip box is arranged in plural, a mother plate in which a plurality of recesses for receiving liquid materials to be dispensed are formed at a certain interval, a mother plate palette on which the mother plate is arranged in plural, a dispense plate in which a plurality of recesses for receiving the dispensed liquid materials are formed at a certain interval, a dispense plate palette on which the dispense plate is arranged in plural, and a tip aligner holding high pipette alignment accuracy in the dispensing head, wherein the column and row numbers in an array of the recesses formed in the dispense plate for receiving the dispensed liquid materials are integer times the column and row numbers in an array of the pipettes in the dispensing head, respectively, wherein intervals between the pipettes in adjacent columns and between the pipettes in adjacent rows in the dispensing head are integer times intervals between the recesses in adjacent columns and between the recesses in adjacent rows in the dispense plate, respectively, and wherein the tip aligner has recesses in number equal to or larger than the number of the pipettes in the dispensing head at the same interval as that between the pipettes.

Advantages of the Invention

According to the present invention, by replacing the dispensing head, samples under different conditions can be prepared on one dispense plate by using one dispensing apparatus. Also, waste liquid materials can be minimized. On that occasion, by changing the amount of the liquid material discharged from the dispenser, samples can be prepared at composition ratios varying over various levels.

Further, by preparing a plurality of dispensing heads including the pipettes arranged thereon in the same number, even when the pipette head requires maintenance, the dispensing apparatus can be continuously operated with replacement of the dispensing head without interrupting the dispending operation for a long time.

BRIEF DESCRIPTION OF THE INVENTION

Figure 1:
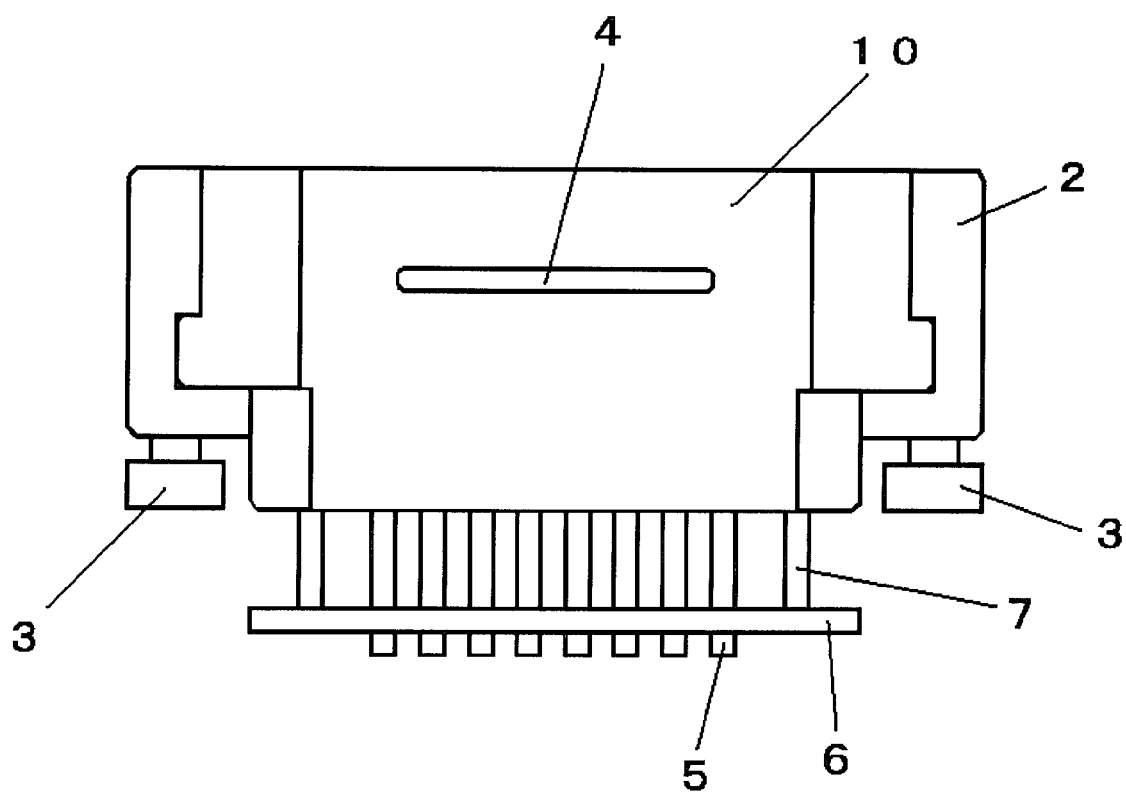
FIG. 1 is a front view of a dispensing head (having pipettes of 8 columns×12 rows in a horizontal array) in a dispensing apparatus according to the present invention.

REFERENCE NUMERALS 1 dispensing head
2 body holder
3 body connector
4 body part grip
5 pipette
6 tip release plate
7 post
8 tip
10 head body part
11 dispense plate
12 dispense plate palette
15 vertical drive mechanism
16 horizontal drive mechanism
17 apparatus bench
18 horizontal drive stage
19 drive mechanism supporting post
20 test tube
21 tip aligner
22 mother plate stage
23 dispense plate stage
24 trash box
26 tip box
27 tip box palette
28 mother plate
29 mother plate palette
31 pipette head
32 pipette head connector
33 pipette head holder
44 head holder
45 ball screw
51 pipette body
52 plunger
53 release plate pushing member
54 spring

BEST MODE FOR CARRYING OUT THE INVENTION

Based on a basic structure in which a dispensing head is mounted to a robot movable in the horizontal and vertical directions, liquid materials in test tubes are sucked by a plurality of tips attached to pipettes in the dispensing head, and the sucked liquid materials are poured onto a dispense plate while moving the dispensing head in the horizontal and vertical directions, the present invention is realized by adding a specific dispensing head to the basic structure. In other words, the dispensing head according to the present invention has such a structure that it is divided into a body part and a pipette head and only the pipette head is movable in the up-and-down direction. Further, the dispensing head is replaceable. The structure of the dispensing head according to the present invention will be described in detail below.

(Structure of Dispensing Head)

As shown in FIGS. 5 through 8, a dispensing head 1 comprises a body part 10 including pipettes 5, a pipette head 31 disposed above the body part 10, and a tip release plate 6 disposed below the body part 10. A body grip (pull) 4 is formed to extend forward from an upper end portion of the body part 10.

Figure 9:
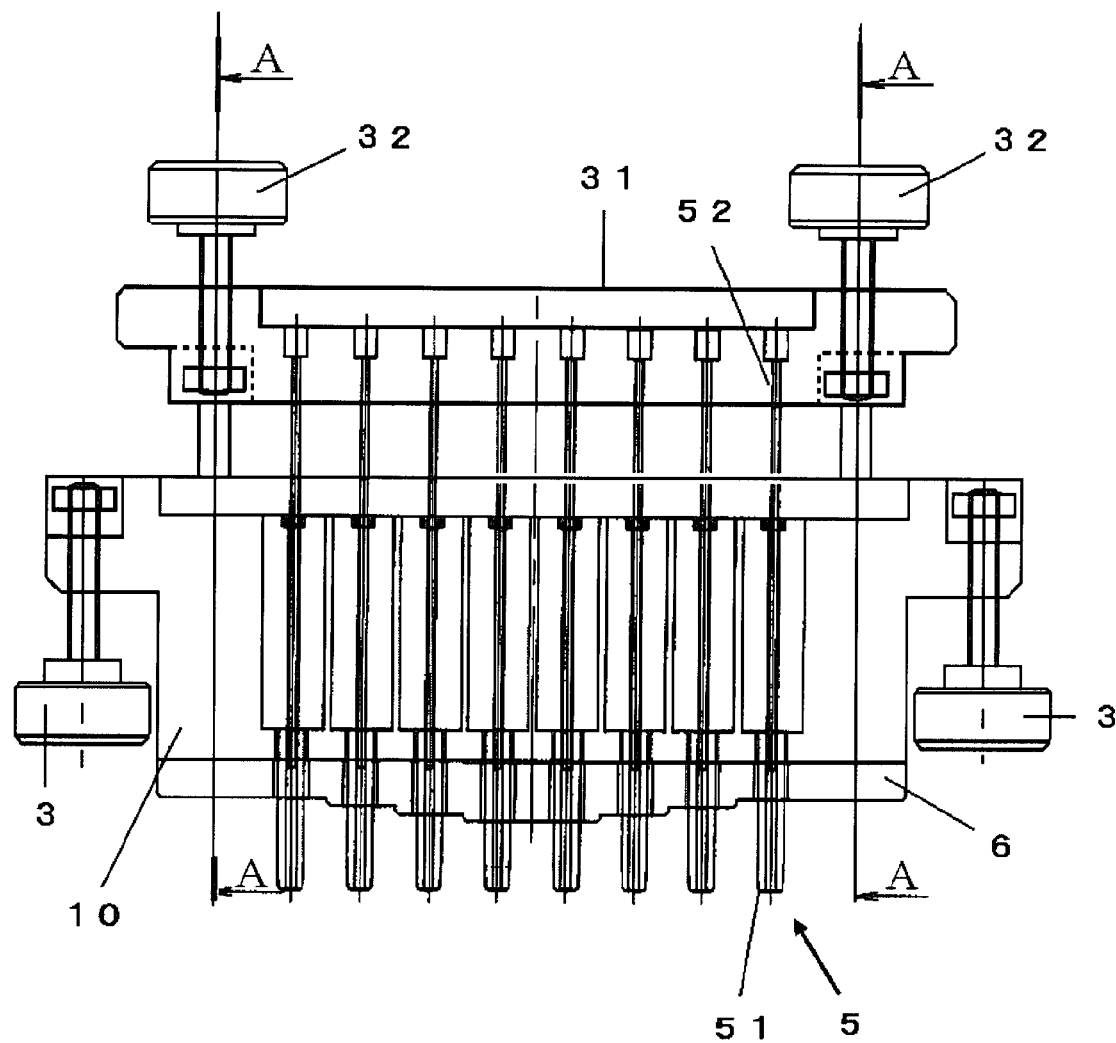
FIG. 9 is an explanatory view of a tip releasing mechanism.

Each of the pipettes 5 comprises, as shown in FIG. 9, a pipette body 51 and a plunger 52 which is movable to advance and retract through a hole formed in the pipette body. All the plungers 52 are connected to the pipette head 31 such that the plungers 52 are moved up and down in conjunction with the pipette head 31.

Figure 7:
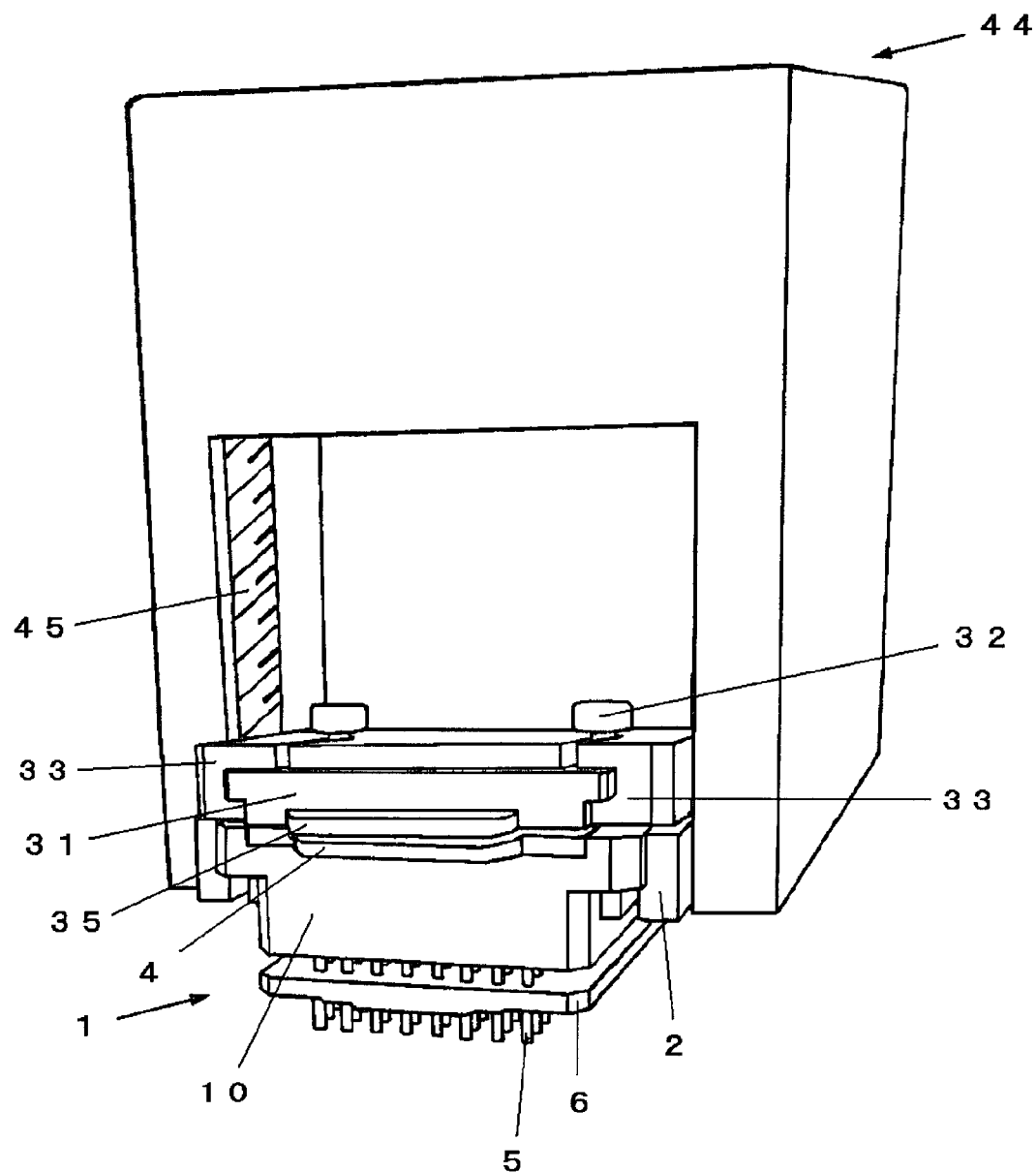
FIG. 7 is an explanatory perspective view in a state where tips are released in the dispensing head according to the present invention.
Figure 8:
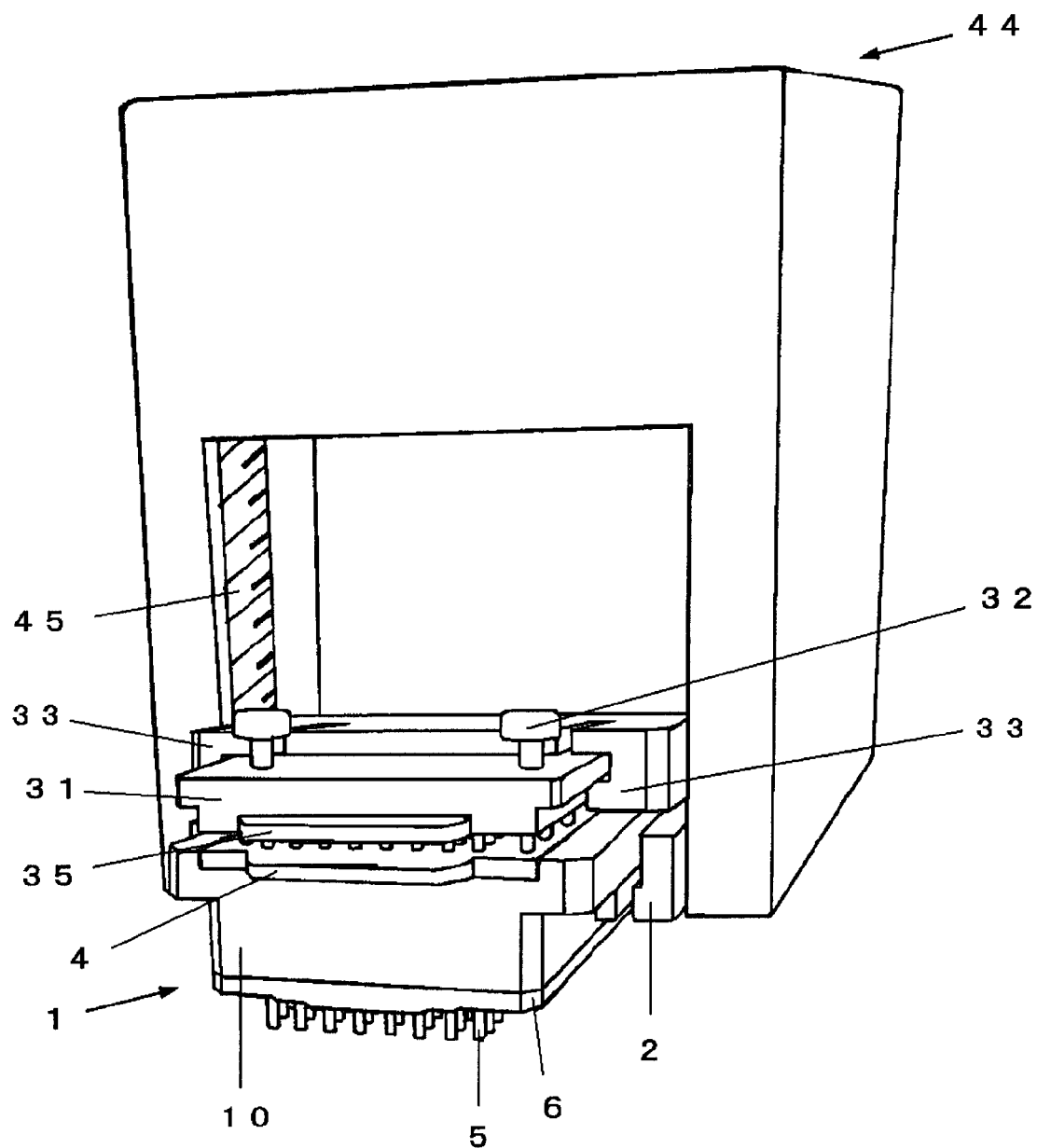
FIG. 8 is an explanatory perspective view in a state where the dispensing head according to the present invention is removed.

The dispensing head 1 comprises body connectors 3 (see FIG. 1) and pipette head connectors 32. The dispensing head 1 is connected to the body holder 2 by the body connectors 3, and it is connected and fixed to a head holder 44 by the pipette head connectors 32. FIG. 8 shows a state where the dispensing head 1 is withdrawn toward a viewer looking at the drawing sheet with the aid of the body part grip 4 by loosening both the body connectors 3 and the pipette head connectors 32. Thus, the pipette head 31 and the body part 10 can be withdrawn and removed as an integral unit. In one embodiment, the pipette head 31 has a grip 35, and the grip 35 and the body part grip 4 may be combined to form one grip when the pipette head 31 and the head body part 10 are abutted against each other, as shown in FIG. 7.

The head holder 44 is connected to a vertical moving mechanism (Z-axis moving means) for a pouring device, and the vertical moving mechanism is connected to a horizontal moving mechanism (XY moving means) for the pouring device. With such a structure, the dispensing head 1 fixed to the head holder 44 can be moved in the X-, Y- and Z-directions within the pouring device.

The vertical moving mechanism and the horizontal moving mechanism are each constituted by a known moving means in which a rotating motor, such as a stepping motor or a servo motor, and a slider for moving the head holder and the head body part in the vertical and horizontal directions are coupled to each other through a ball screw. By arranging the vertical drive mechanism in addition to the slider of the horizontal drive mechanism, the head body part is constituted to be movable in the vertical and horizontal planes. Alternatively, the vertical drive mechanism and the horizontal drive mechanism may be each constituted by using a linear motor which is linearly movable on a plane.

A pipette head holder 33 is coupled to a ball screw 45 such that the pipette head holder 33 is movable in the Z-direction, i.e., up and down. Accordingly, the pipette head 31 fixed to the pipette head holder 33 is also moved up and down together with the pipette head holder 33. In other words, a pipette head moving mechanism is constituted by a known moving means in which a rotating motor, such as a stepping motor or a servo motor, and a slider for moving the pipette head up and down are coupled to each other through a ball screw. The pipette head 31 is moved in the vertical direction together with the rotation of the rotating motor. The pipette head moving mechanism may be constituted by using a linear motor capable of linearly moving on a plane such that the slider including the pipette head is smoothly moved on a slide base.

The number of mounted pipettes can be changed depending on the dispense plate used. Typical examples of the dispensing head include 2 pipettes (1 column×2 rows), 6 pipettes (1 column×6 rows), 24 pipettes (2 columns×12 rows), 36 pipettes (3 columns×12 rows), 48 pipettes (4 columns×12 rows), and 96 pipettes (8 columns×12 rows).

Generally, each pipette has a tapered distal end. By setting the pitch of an array of test tubes, which receive the poured liquid material, two times the pitch of the pipettes (i.e., by setting the interval between the test tubes in the array to ½ of the interval between the pipette tips in the array) in consideration of such a pipette shape, the liquid material can be poured so as to prepare samples in four-time number. The pitch of the array of test tubes may be set to be other integer (three or more) times the pitch of the pipettes.

In that case, since higher pitch accuracy is required for alignment of the pipettes, a tip aligner is desirably provided.

(Operation)

(1) Basic Operation

First, the dispensing head 1 is positioned by the XY moving means such that the dispensing head 1 is located above the desired plate. Thereafter, tips 8 attached to respective distal ends of the pipettes 5 are descended by the Z-axis moving means and are dipped in a liquid prepared in the recesses formed in the mother plate. Then, the pipette head 31 is ascended by the pipette head moving mechanism such that the liquid is sucked into the tips (see FIG. 5).

Subsequently, the dispensing head 1 is ascended by the Z-axis moving means so as to position the distal ends of the tips 8 above the dispense plate 11. The dispensing head 1 is then moved by the XY moving means to the desired dispense plate 11.

Figure 6:
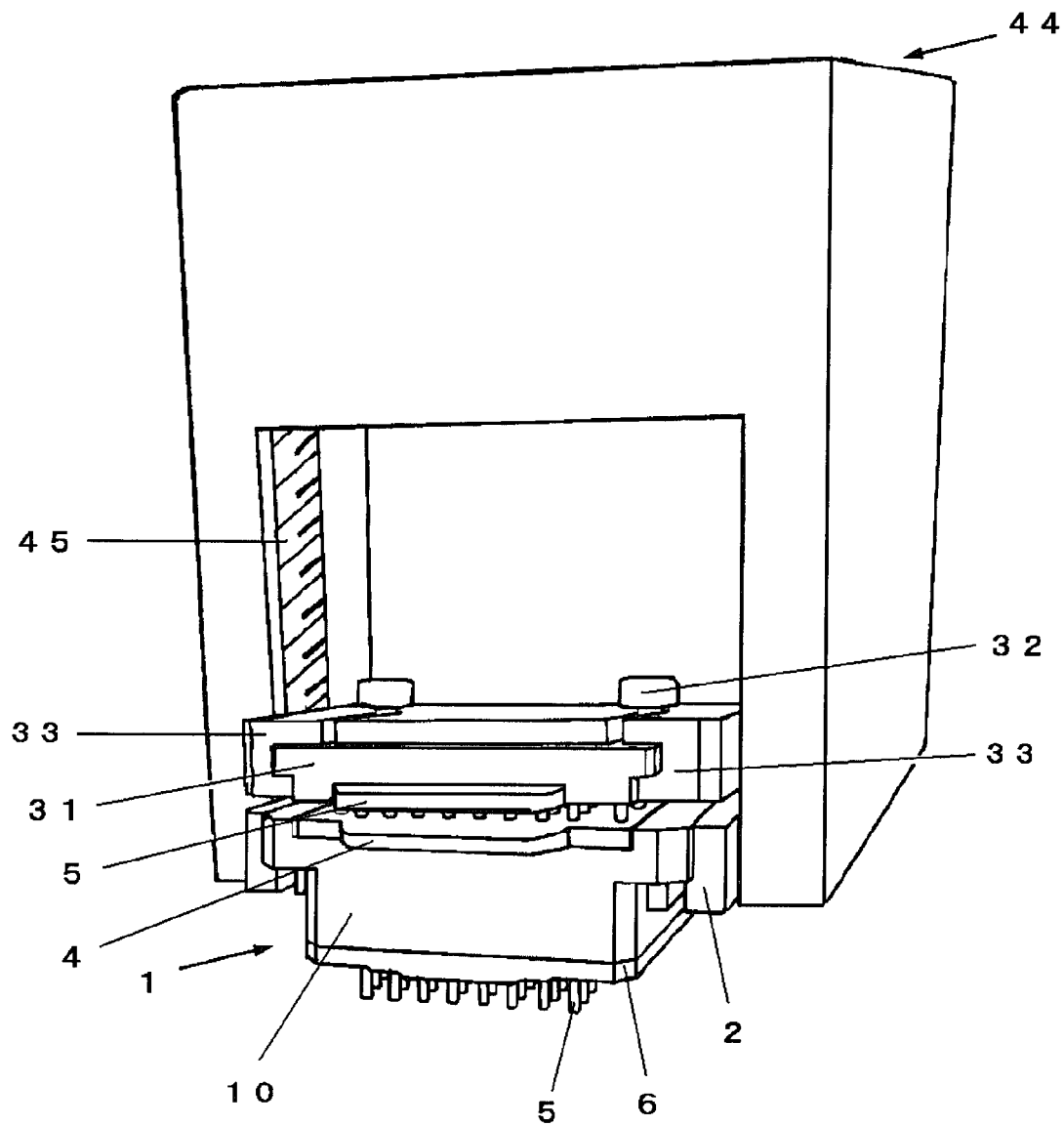
FIG. 6 is an explanatory perspective view in a state where the liquid material is discharged in the dispensing head according to the present invention.

Thereafter, the tips 8 are descended by the Z-axis moving means to enter recesses formed in the dispense plate 11, and the pipette head 31 is descended by the pipette head moving mechanism to discharge the liquids in the tips 8 (see FIG. 6). Because the pipette head 31 is connected to all the plungers 52 as shown in FIG. 9, the liquid materials in the tips 8 are discharged with all the plungers 52 being descended in conjunction with the pipette head 31.

(2) Tip Releasing/Discarding

After discharging the liquids in the tips 8, the dispensing head 1 is ascended by the Z-axis moving means so as to position the distal ends of the tips 8 above the dispense plate 11. The dispensing head 1 is then moved by the XY moving means to a tip discard position.

Figure 10:
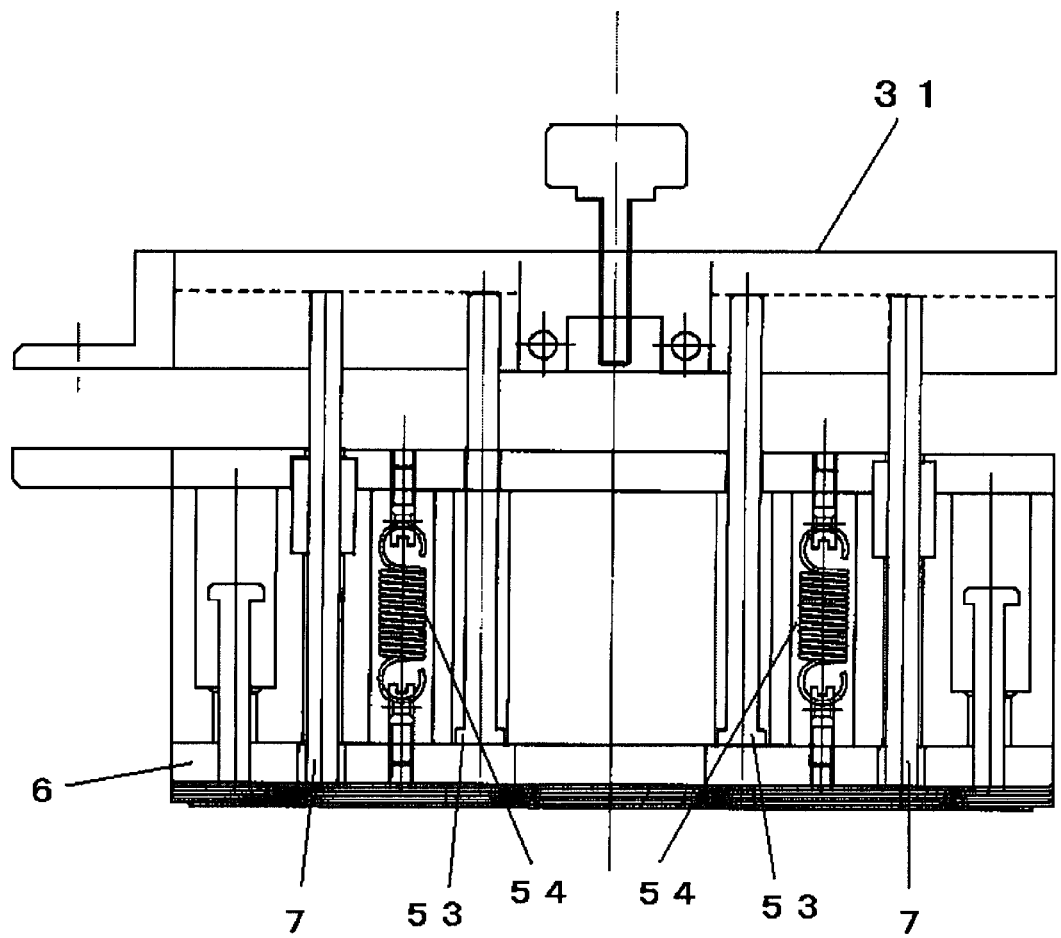
FIG. 10 is a sectional view of the tip releasing mechanism taken along AA in FIG. 9.

In the dispensing head 1 having moved to the tip discard position, the pipette head 31 are further descended to lower the tip release plate 6 so that the tips 8 are released or detached from the pipettes 5 and are dropped into a trash box 24. A tip releasing mechanism will be described in more detail below with reference to FIGS. 9 and 10.

(Tip Releasing Mechanism)

As shown in FIG. 9, each plunger 52 immediately before the tip releasing is located at a position where it is slightly advanced downward from its most downwardly advanced position in the liquid sucking and discharging operations. In that position, one end of each of release plate pushing members 53 contacts with the tip release plate 6. The other end of the release plate pushing member 53 is fixed to the pipette head 31. Therefore, when the pipette head 31 is moved to advance and retract by the pipette head moving mechanism, each release plate pushing member 53 is also moved to advance and retract. At that time, the release plate pushing member 53 pushes the tip release plate 6 such that the tip release plate 6 is moved away from the body part 10. The tip release plate 6 having moved away from the body part 10 is further descended to contact with upper ends of the tips. With a further descent of the tip release plate 6, the tips are released from the pipette body 51. Each pipette 5 and each tip 8 are fixed to each other with a tip end of the pipette body 51 just inserted in a hole formed in the tip. Therefore, the tip can be easily released from the pipette body 51 with the descent of the tip release plate 6.

For the purpose of more easily releasing the tips, as shown in FIG. 9, a surface of the tip release plate 6 on the side facing the tips is preferably formed to have steps of which thicknesses are gradually increased from the peripheral toward the center. More specifically, the provision of those steps is advantageous in the following point. When the tip release plate 6 is descended, the tips are released in a successive manner from a central area toward an outer periphery such that the tips attached to the distal ends of the pipette bodies 51 arranged in the central area are first released and the tips located in an area outwardly adjacent to the central area are then released. If the tip release plate 6 is formed as a flat plate without including the steps, stationary frictional forces generated upon releasing of the tips are imposed at a time in amount corresponding to the total number of tips. This means that a large force overcoming the stationary frictional forces has to be produced at a time and the pipette head moving mechanism is required to produce such a large force. Accordingly, the load applied to the pipette head moving mechanism can be reduced by releasing the tips in a successive manner.

After releasing the tips, when the pipette head 31 is retracted by the pipette head moving mechanism, the release plate pushing member 53 fixed to the pipette head 31 is also retracted together. At that time, by the action of springs 54 each interconnecting the tip release plate 6 and the body part 10, the tip release plate 6 is moved toward a position where it contacts with the body part 10, while always keeping contact with the distal end of the release plate pushing member 53. When the distal end of the release plate pushing member 53 comes into the body part 10, the release plate pushing member 53 and the tip release plate 6 are spaced from each other. Simultaneously, the tip release plate 6 contacts with the body part 10 and stops its movement (see FIG. 10). In such a state, the tip release plate 6 is held fixed to the body part 10 by the action of the springs 54.

While the present invention will be described in more detail below in connection with embodiments, the present invention is in no way limited to the following embodiments.

EMBODIMENT 1

Figure 2:
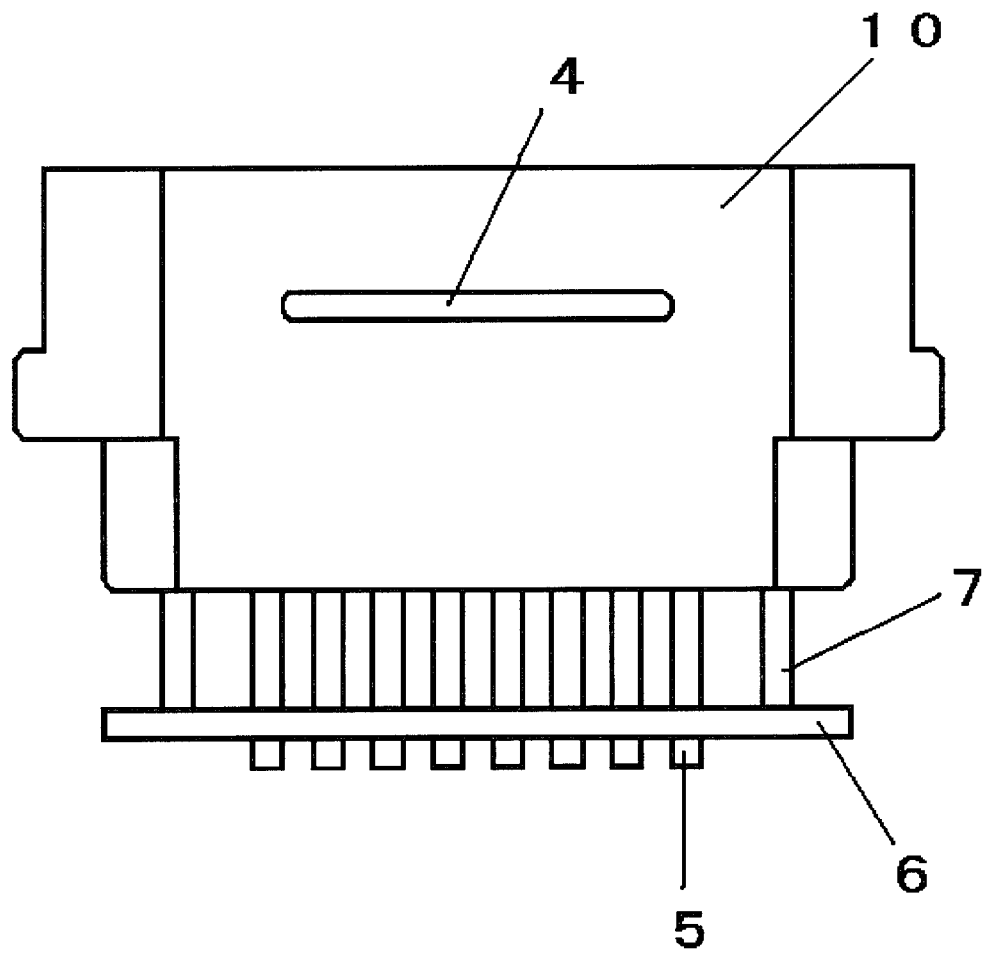
FIG. 2 is a front view of the dispensing head in a state where the dispensing head is removed from a body holder.
Figure 3:
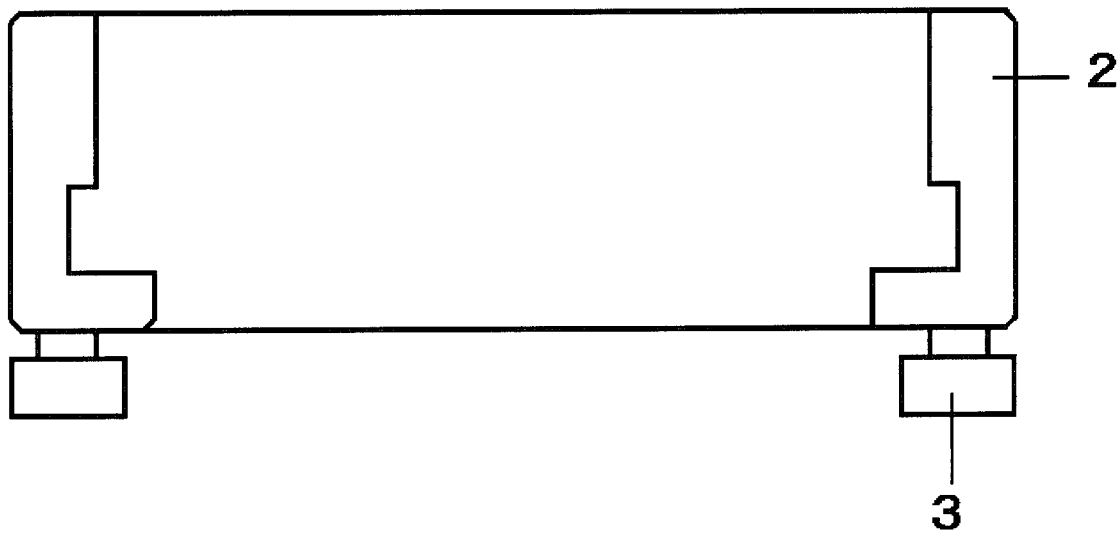
FIG. 3 is a front view of the body holder in a state where the dispensing head is removed.
Figure 4:
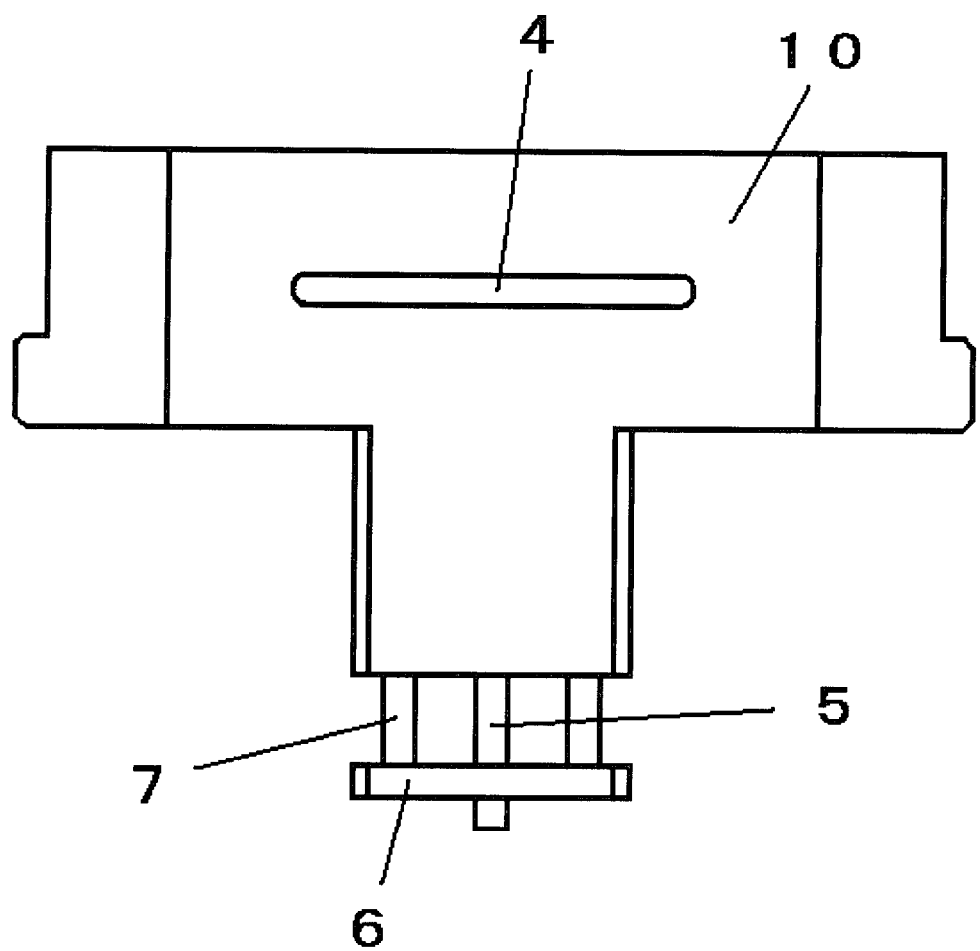
FIG. 4 is a front view of a dispensing head (having pipettes of 1 column×12 rows in a horizontal array) according to the present invention.
Figure 5:
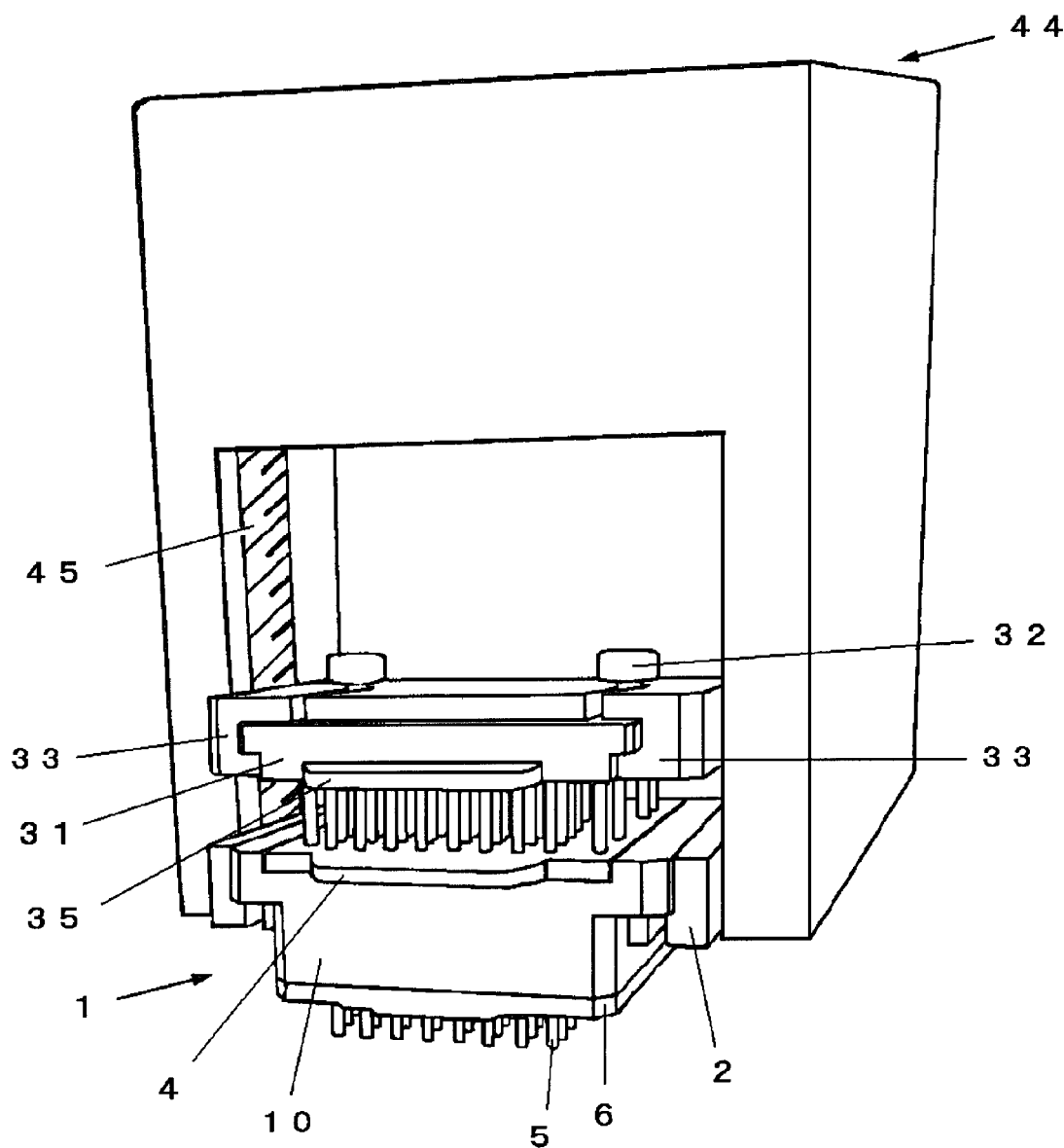
FIG. 5 is an explanatory perspective view in a state where a liquid material is sucked in the dispensing head according to the present invention.

As shown in FIG. 1, the dispensing head 1 used in the dispensing apparatus of this embodiment comprises the body holder 2, the body connectors 3, the body grip 4, the pipettes 5 to which the tips are attached, the tip release plate 6 for releasing (detaching) the tips from the pipettes, and posts 7. The dispensing head has 96 pipettes (8 columns×12 rows) and is mounted to the body holder 2. FIG. 2 shows a state where the dispensing head 1 is removed from the body holder 2 by loosening the body connectors 3, and FIG. 3 shows the body holder 2 from which the dispensing head 1 is removed. FIG. 4 is a front view of a dispensing head having 12 pipettes (1 column×12 rows), which is also mounted to the body holder 2. It is to be noted that the pipette head 31 is omitted in FIGS. 1-4.

Figure 11:
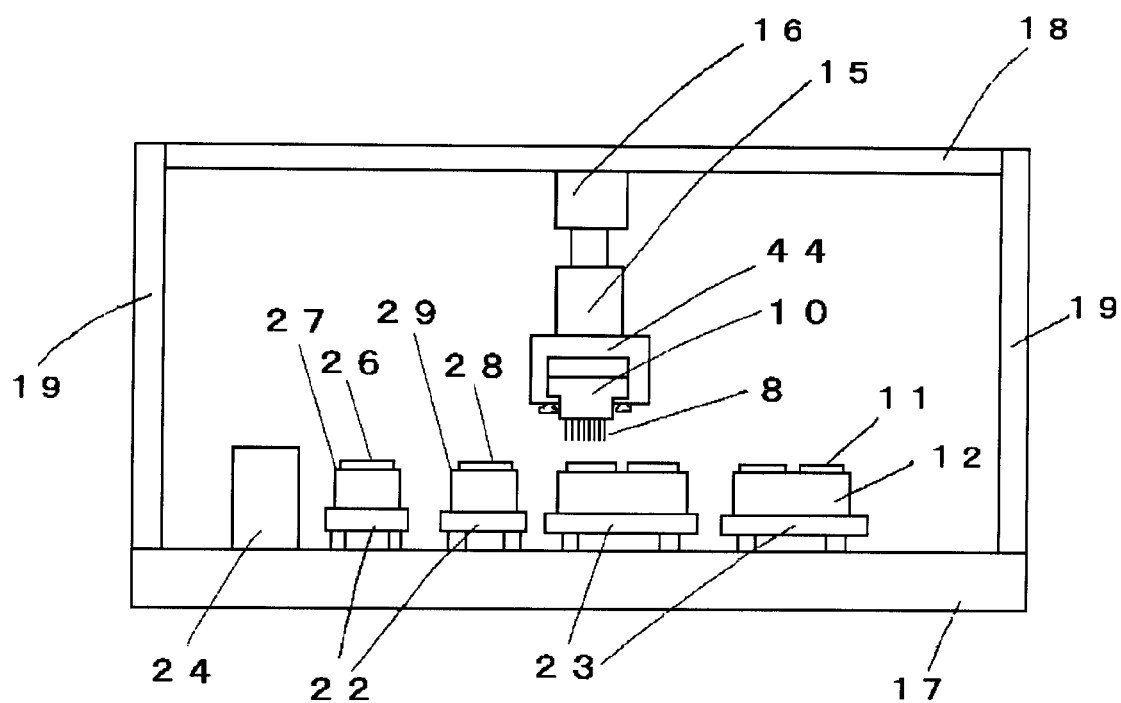
FIG. 11 is a schematic view showing the structure of a dispensing station according to Embodiment 1.

FIG. 11 shows a state where the dispensing head 1 is mounted to the head holder 44. The head holder 44 is coupled to a drive mechanism 15 for moving the head holder 44 in the vertical direction (i.e., in the Z-axis direction) and to a drive mechanism 16 for moving the head holder 44 in the horizontal direction (i.e., in the X- and Y-axis directions). In FIG. 11, reference numeral 11 denotes a dispense plate on which test tubes for receiving poured liquid materials are arrayed; 17 denotes a bench on which the dispensing apparatus is supported; 18 denotes a stage for moving the holder 44 in the horizontal direction (i.e., in the X- and Y-axis directions); 19 denotes a post for supporting the moving mechanisms; 21 denotes a tip aligner for aligning the distal ends of the tips; 22 denotes a stage with a structure allowing a tip box palette or a mother plate palette to be withdrawn back and forth; 23 denotes a stage with a structure allowing a dispense plate palette to be withdrawn back and forth; 24 denotes a trash box into which the tips 8 detached from the dispensing head 1 are discarded after the liquid pouring operation using the tips 8; 26 denotes a tip box in which the tips 8 are stored; 27 denotes a tip box palette on which the tip box 26 is fixedly supported; 28 denotes a mother plate on which test tubes containing the liquid materials to be poured are arrayed; and 29 denotes a mother plate palette on which the mother plate is fixedly supported.

Figure 12:
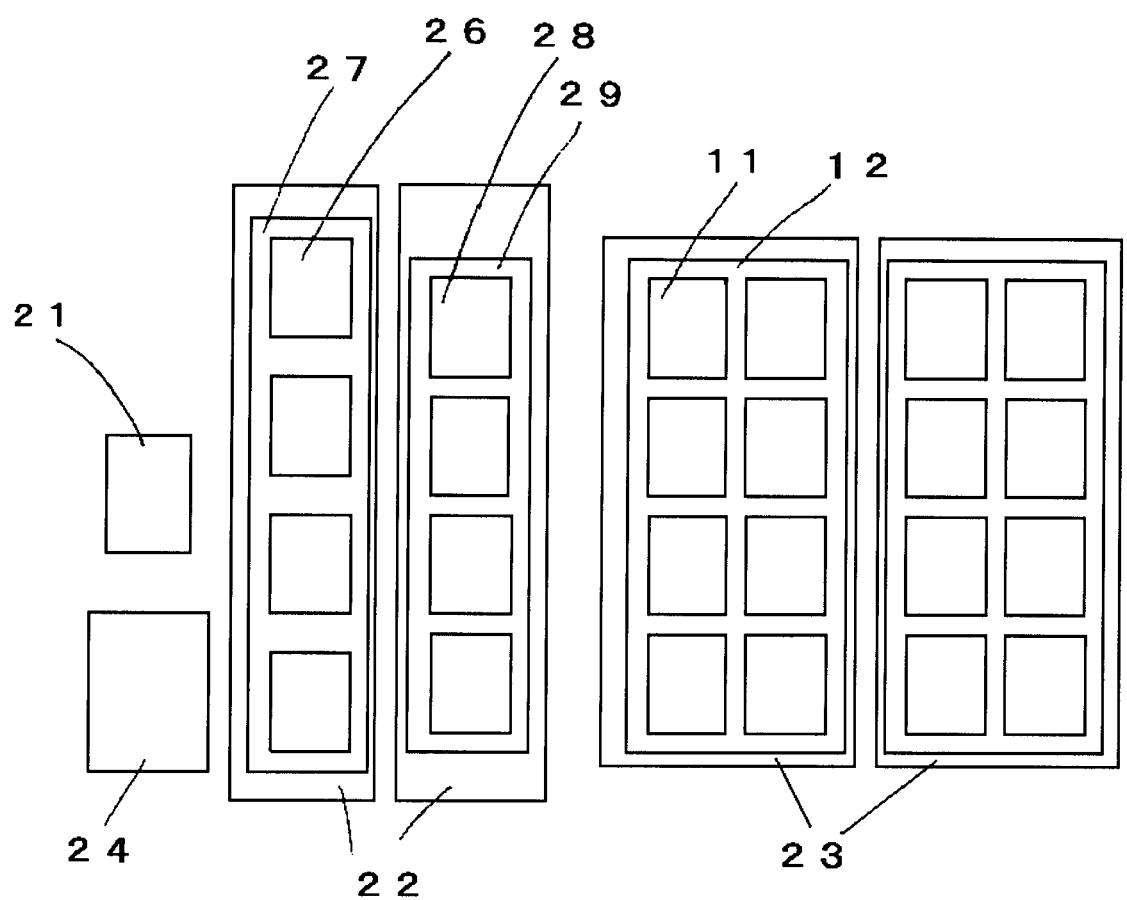
FIG. 12 is an explanatory plan view of various plates used in Embodiment 1.
Figure 13:
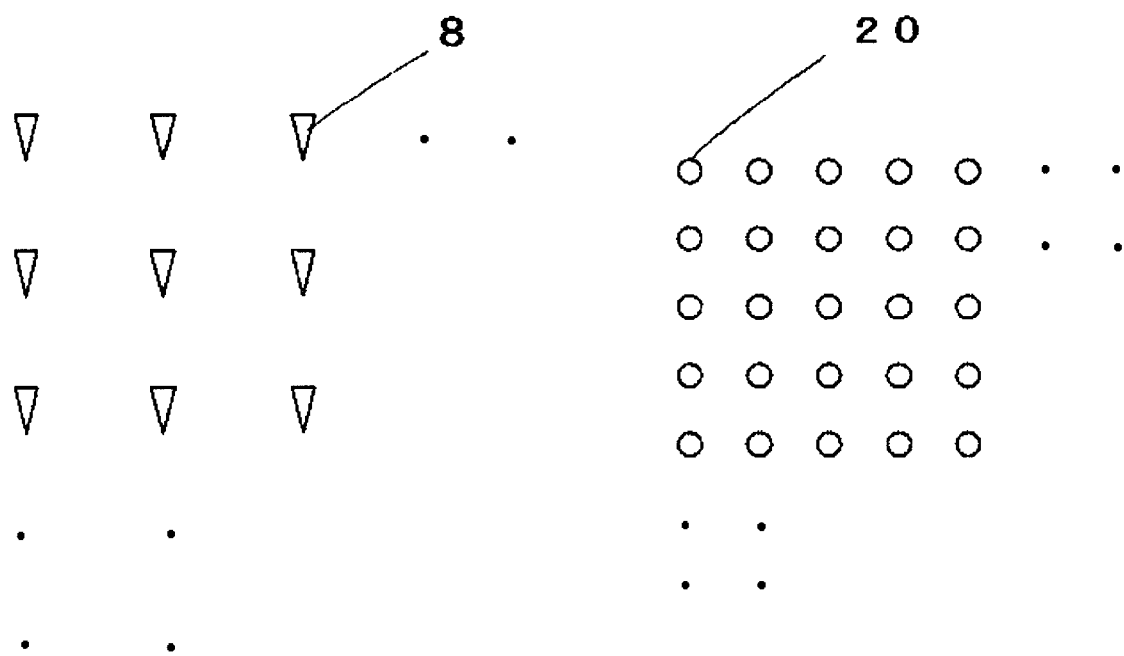
FIG. 13 is an explanatory plan view illustrating the pitch of the tips and the pitch of test tubes.

As shown in FIG. 12, four tip boxes 26 are disposed on the tip box palette 27 such that the tips can be arrayed in four patterns on one tip box palette 27. The tips can be arrayed in number 96 in each of all the four tip boxes 26, or they can also be arrayed in a different number (e.g., 12) corresponding to the dispensing head having a different number of pipettes. Four mother plates 28 including test tubes arrayed thereon are disposed on the mother plate palette such that different kinds of liquid materials in the same number as the mother plates can be poured.

Because the amount of each liquid material discharged to the dispense plate 11 can be changed per cycle of operations, a mixing ratio of the four kinds of liquid materials can also be changed by properly programming the amount of each liquid material discharged in each pouring operation.

(Operation)

The following description is given of the dispensing operation which is carried out by using four sets of 96 tips 8.

The dispensing head 1 is moved to a position above the tip boxes 26 by the X, Y-axis horizontal drive mechanism 16. The dispensing head 1 is then moved downward by the vertical drive mechanism 15 such that the tips are mechanically held on the dispensing head from one of the four tip boxes 26. Thereafter, the dispensing head 1 is moved upward by the vertical drive mechanism 15.

On the mother plate 28, the test tubes are arrayed in the same number and at the same pitch as the tips 8. The dispensing head 1 is moved downward such that all the tips come into the respective test tubes on the mother plate 28 and suck the liquid materials therein. Then, the dispensing head 1 is moved upward by the vertical drive mechanism 15 and is further moved in the horizontal direction to be positioned above the dispense plate 11. Subsequently, the dispensing head 1 is moved downward and the preset amounts of the liquid materials are discharged for pouring into the respective test tubes on the dispense plate 11. After the end of the predetermined pouring operation, the dispensing head 1 is moved to a position above the trash box 24. The tip release plate 6 is moved downward to release the tips 8, whereby the spent tips 8 are dropped into the trash box 24. A series of the above-described operations are performed by properly programming a robot control unit and a dispenser control unit.

The dispensing apparatus of this embodiment has a layout including the four tip boxes 26 each having 96 tips, the four mother plates 28 each having 96 test tubes, and the sixteen dispense plates 11 each including 96 test tubes. A total number of test tubes set on all the dispense plates 11 is 1536 (96×16).

By using the dispensing apparatus of this embodiment, 1536 samples can be prepared by one cycle of operations.

EMBODIMENT 2

Because the distal ends of the tips 8 are just required in Embodiment 1 to enter respective test tubes 20 on the dispense plate 11, the interval between the test tubes 20 can be further reduced. In this Embodiment 2, the test tubes 20 are arrayed at the interval that is a half the interval between the tips 8, to thereby increase the number of test tubes arrayed on the dispense plate. In other words, 384 test tubes (96×4; 16 columns×24 rows) are arrayed on one dispense plate having the same area as in Embodiment 1. Such an arrangement is effective in avoiding the disadvantages of excessively increasing the number of pipettes in match with the interval between the test tubes, reducing the dispensing accuracy with the use of smaller pipettes and tips, and causing a difficulty in alignment of the tips. To be adapted for the reduction of the interval between the test tubes to ½, the accuracy in alignment of the tips 8 has to be improved. Such a problem can be overcome by providing the tip aligner 21, as shown in FIG. 12, for an improvement of the accuracy in alignment of the tips 8.

In this embodiment, a plurality of holes in number corresponding to the pipettes are formed in an upper surface of the tip aligner 21. The accuracy in alignment of the tips 8 is improved by inserting, in respective holes, the tips 8 attached to the pipettes 5.

In this embodiment, a number 384 of test tubes 20 are arrayed on the dispense plate 11, while 96 tips are attached to the dispensing head 1. Therefore, four discharging operations are required to complete the dispensing for one dispense plate 11 (the amount of the discharged liquid material may be changed for each discharging operation).

With such an arrangement, samples can be prepared in number 96 at one level of the discharge amount per operation with four levels at maximum. Therefore, this embodiment including sixteen dispense plates 11 can prepare samples at 64 levels of the discharge amount by one cycle of operations.

Since the number of test tubes on each dispense plate 11 is 384 and the number of the dispense plates 11 is 16, a total 6144 of data can be prepared by one cycle of operations.

The invention claimed is:
1. A high-speed automatic dispensing apparatus with a replaceable dispensing head, comprising:
a dispensing head including a plurality of pipettes, a pipette head to which one end of a plunger extending to pass through each pipette is fixed, and a head body part abutting against the pipette head and allowing the pipettes to pass therethrough, a head holder to which the dispensing head is detachably fixed, a pipette head moving mechanism vertically moving the pipette head, a drive mechanism horizontally and vertically moving the head holder, and a tip releasing plate abutting against a lower surface of said head body part and allowing said pipettes to pass therethrough, and configured to move downward, thereby releasing tips from said pipettes, wherein said head holder comprises a pipette head holder to which the pipette head is detachably fixed, and a body holder to which the head body part is detachably fixed, wherein the pipette head is vertically moved by vertically moving the pipette head holder with the pipette head moving mechanism, wherein said head body part, said pipette head and said tip releasing plate are withdrawn and removed as an integral unit from the head holder, wherein said pipette head includes a pushing member to move said tip releasing plate downward, one end of said pushing member being fixed to the pipette head, a body of said pushing member being inserted into the head body part and passing therethrough, said pushing member having such a length that another end of said pushing member abuts against said tip releasing plate at a position where said pipette head is advanced beyond a position for discharging a liquid material, and wherein said tip releasing plate and said head body part are interconnected by springs.

2. A high-speed automatic dispensing apparatus with a replaceable dispensing head according to claim 1, wherein said pipette head and said head body part have respective grips which are combined to form one grip.

3. A dispensing station comprising:

a high-speed automatic dispensing apparatus with a replaceable dispensing head, the dispensing head comprising a dispensing head including a plurality of pipettes arranged in a column and row, a pipette head to which one end of a plunger extending to pass through each pipette is fixed, and a head body part abutting against the pipette head and allowing the pipettes to pass therethrough, a head holder to which the dispensing head is detachably fixed, a pipette head moving mechanism vertically moving the pipette head, and a drive mechanism horizontally and vertically moving the head holder, a tip box on which a plurality of tips to be attached to the plurality of pipettes are arranged at a certain interval, a tip box palette on which said tip box is arranged in plural, a mother plate in which a plurality of recesses for receiving liquid materials to be dispensed are formed at a certain interval, a mother plate palette on which said mother plate is arranged in plural, a dispense plate in which a plurality of recesses for receiving the dispensed liquid materials are formed at a certain interval in a column and row, a dispense plate palette on which said dispense plate is arranged in plural, and a tip aligner separately located from the dispensing head and having holes into which the tips attached to the plurality of pipettes are to be inserted, wherein numbers of the column and row of the recesses formed in the dispense plate for receiving the dispensed liquid materials are integer times numbers of the column and row of the pipettes in said dispensing head, respectively, wherein intervals between the adjacent pipettes in said dispensing head are integer times intervals between the adjacent recesses in said dispense plate, respectively, wherein the holes of said tip aligner are arranged in number equal to or larger than the number of the pipettes in the dispensing head at same intervals as the intervals between the adjacent pipettes, wherein the holes of said tip aligner are formed with high pipette alignment accuracy to improve alignment of the tips attached to the plurality of pipettes when the tips are inserted into the holes, wherein said head holder comprises a pipette head holder to which the pipette head is detachably fixed, and a body holder to which the head body part is detachably fixed, wherein the pipette head is vertically moved by vertically moving the pipette head holder with the pipette head moving mechanism, wherein said head body part, said pipette head and said tip releasing plate are withdrawn and removed as an integral unit from the head holder, wherein said dispensing head comprises a tip releasing plate abutting against a lower surface of said head body part and allowing said pipettes to pass therethrough, and the tips are released from said pipettes by moving said tip releasing plate downward, wherein said pipette head includes a pushing member to move said tip releasing plate downward, one end of said pushing member being fixed to the pipette head, a body of said pushing member being inserted into the head body part and passing therethrough, said pushing member having such a length that another end of said pushing member abuts against said tip releasing plate at a position where said pipette head is advanced beyond a position for discharging a liquid material, and wherein said tip releasing plate and said head body part are interconnected by springs.

4. A dispensing station according to claim 3, wherein said tip releasing plate of said high-speed automatic dispensing apparatus has a stepped surface whose thickness varies from opposite end areas in the lengthwise direction toward a central area.

5. A dispensing station according to claim 3, wherein said pipette head and said head body part have respective grips which are combined to form one grip.

6. The high-speed automatic dispensing apparatus with a replaceable dispensing head according to claim 1, wherein the steps on the surface of said tip releasing plate are formed symmetrically about the central area in the lengthwise direction.

7. The high-speed automatic dispensing apparatus with a replaceable dispensing head according to claim 1, wherein said tip releasing plate extends in a horizontal direction, and wherein said tip releasing plate is configured to move vertically downward while maintaining the horizontal direction.

8. The high-speed automatic dispensing apparatus according to claim 1, wherein said tip releasing plate has a stepped surface whose thickness varies from opposite end areas toward a central area in a lengthwise direction of said tip releasing plate.

9. The high-speed automatic dispensing apparatus according to claim 1, wherein said pushing member is provided at opposite sides with respect to the plunger in a horizontal direction.

10. The high-speed automatic dispensing apparatus according to claim 3, wherein said pushing member is provided at opposite sides with respect to the plunger in a horizontal direction.

* * * * *